United States Patent [19]

De Woskin

[11] 4,308,010
[45] Dec. 29, 1981

[54] NECK PAD MATERIAL AND A METHOD FOR ITS MANUFACTURE

[75] Inventor: Irvin S. De Woskin, Manchester, Mo.

[73] Assignee: Orthoband Company, Inc., Barnhart, Mo.

[21] Appl. No.: 211,504

[22] Filed: Dec. 1, 1980

Related U.S. Application Data

[63] Continuation-in-part of Ser. No. 934,707, Aug. 21, 1978, abandoned, which is a continuation-in-part of Ser. No. 714,477, Aug. 16, 1976, abandoned.

[51] Int. Cl.³ ............................................. A61C 7/00
[52] U.S. Cl. .................................................... 433/5
[58] Field of Search ........................................... 433/5

[56] References Cited

U.S. PATENT DOCUMENTS 2,874,468  2/1969  De Woskin .......................... 433/5
4,130,681  12/1978  De Woskin .......................... 433/5

Primary Examiner—Robert Peshock
Attorney, Agent, or Firm—Senniger, Powers, Leavitt and Roedel

[57] ABSTRACT

Neck pad material in the form of tape adapted to be cut to selected lengths for use with orthodontic appliances or the like, comprising at least three strips of heat-sealable material seamed together at their sides for forming pad material, with an intermediate strip being of heavier loft than the outer strips for providing a cushioning effect. The pad material has areas of heat seal extending transversely thereof from one edge of the pad material to the other with the areas being spaced at intervals lengthwise of the pad. The pad material is adapted to be cut to form pads of selected length by cutting transversely of the pad material through these areas. A method of making such material is also described.

8 Claims, 7 Drawing Figures

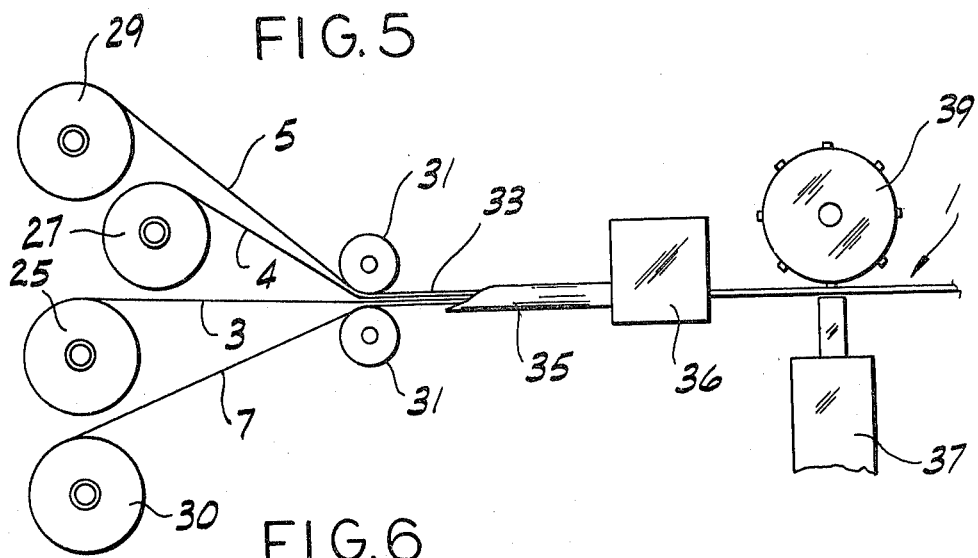
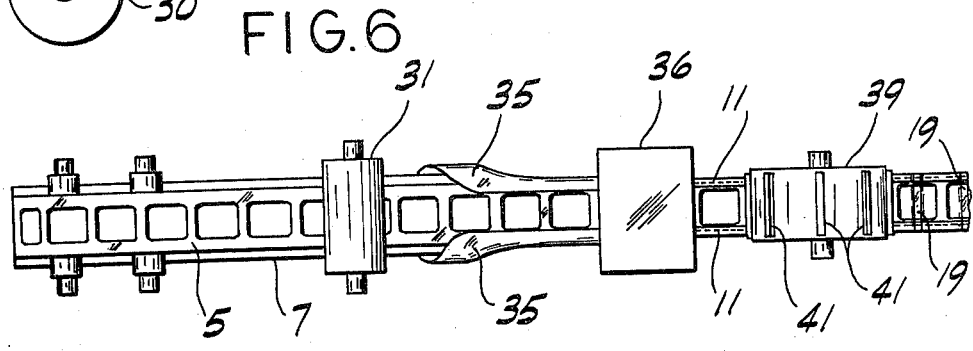
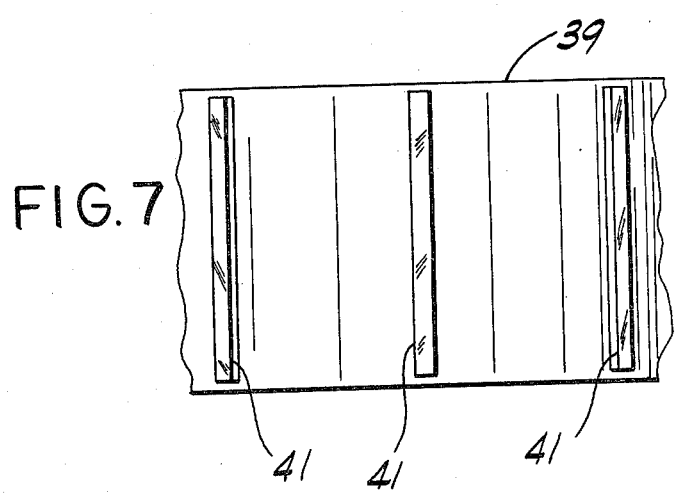

NECK PAD MATERIAL AND A METHOD FOR ITS MANUFACTURE

CROSS-REFERENCE TO RELATED APPLICATION

This is a continuation-in-part of application Ser. No. 934,707, filed Aug. 21, 1978, which is a continuation-in-part of application Ser. No. 714,477, filed Aug. 16, 1976, both now abandoned.

BACKGROUND OF THE INVENTION

This invention relates to segmentable neck pad tape material for use with orthodontic appliances.

Neck pads for use with orthodontic appliances such as shown in my U.S. Pat. No. 2,874,468, issued Feb. 24, 1959, have heretofore been either individually formed or have been cut from a continuous composite strip of pad material. In the latter instance, however, it was desirable for each of such individual pads to have its ends overstitched after being segmented from the continuous strip for providing finished edges at the ends of the pad to avoid unravelling and fraying of the pad material.

SUMMARY OF THE INVENTION

Among the several objects of this invention may be noted the provision of improved neck pad material which may be segmented into individual pads of desired length with each pad having finished ends; and the provision of such pad material which is comfortable on the neck and economical to manufacture.

Briefly, the segmentable neck pad material of this invention comprises an intermediate strip of flexible compressible pad material of relatively heavy loft for providing a cushioning effect. A first flexible outer strip on one face of the intermediate strip has a width generally corresponding to the width of the intermediate strip, and a second outer strip on the other face of the intermediate strip has a width greater than the intermediate strip and the first strip and has side margins folded around the side edges of the intermediate strip and overlying the side margins of the first outer strip. The first outer strip has openings spaced at equal intervals along the length of the strip extending between the edges of the side margins of the second outer strip. All three strips are of heat-sealable material and are seamed together along the sides of the pad material. The pad material further has areas of heat seal extending transversely thereof from one edge of the pad material to the other and penetrating through the first outer strip, the intermediate strip and the second outer strip to seam the three strips together at intervals lengthwise of the pad material. The pad material, and particularly the intermediate strip, is compressed and flattened out in these areas, the pad material thus being divided along its length into a series of discrete relatively thick cushiony pad sections separated by the flattened-out areas of heat seal.

The neck pad material is made by combining at least three strips of flexible heat-sealable material, with one strip, constituting an intermediate strip, being disposed between two outer strips and being of compressible pad material of relatively heavy loft for providing a cushioning effect; continuously feeding the resultant composite strip forward; and compressing and heat-sealing the composite strip as it is fed forward to form, without cutting the strip, flattened-out relatively narrow areas of heat seal penetrating through the three strips to seam them together, the areas of heat seal extending transversely of the composite strip from one edge to the other and spaced at intervals lengthwise of the strip whereby the strip is divided along its length into a series of discrete relatively thick cushiony pad sections separated by the flattened-out areas of heat seal, the strip being adapted to be cut to form pads of selected lengths with finished edges by cutting transversely of the strip through the areas of seal.

Other objects and features will be in part apparent and in part pointed out hereinafter.

BRIEF DESCRIPTION OF THE DRAWINGS

FIG. 5 is a side elevation showing how the neck pad material is made;

FIG. 6 is a plan of FIG. 5; and

FIG. 7 is a developed view of the wheel shown in FIG. 6.

Corresponding reference characters indicate corresponding parts throughout the several views of the drawings.

DESCRIPTION OF THE PREFERRED EMBODIMENT

Figure 4:
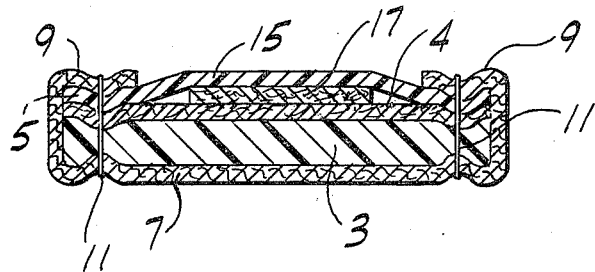
FIG. 4 is an enlarged vertical section on line 4—4 of FIG. 2.

Referring to the drawings, segmentable neck pad material of this invention, generally indicated by the reference numeral 1, is shown to comprise four continuous strips of heat-sealable material seamed together one on top of the other. One of the intermediate strips, designated 3, is of pad material (e.g., natural latex foam rubber, or polyester or polyurethane foam) of relatively heavy loft for providing a cushioning effect and has a strip 4 of facing material applied to its upper (as viewed in FIG. 4) face. This facing strip 4, which has a width corresponding to that of the padding strip 3, is preferably a stretch-knit nylon or polyester fabric or other suitable heat-sealable fabric. Applied to one face of the padding strip 3 over the facing strip 4 is a first outer strip generally designated 5 of sheet plastic (such as polyurethane, polyester or polyolefin film) having a width generally corresponding to the width of the padding strip and extending the full length of the strip.

Indicated at 7 is a second outer strip on the other (lower) face of the intermediate padding strip 3. This outer strip may be of stretch-knit nylon or polyester fabric and has a width somewhat greater than that of the padding strip. The side margins, each designated 9, of the outer strip 7 are folded around the side edges of the padding strip 3 and facing strip 4 to overlie the side margins of strip 5. All four strips 3, 4, 5, 7 are seamed together along the side edges of the pad material by lines of stitching 11, the folded-over side margins 9 of the outer strip 7 being caught by this stitching. It will be understood that the strips could be seamed together along their side edges in other suitable manners (as by lines of heat seal) without departing from the scope of this invention.

Figure 1:
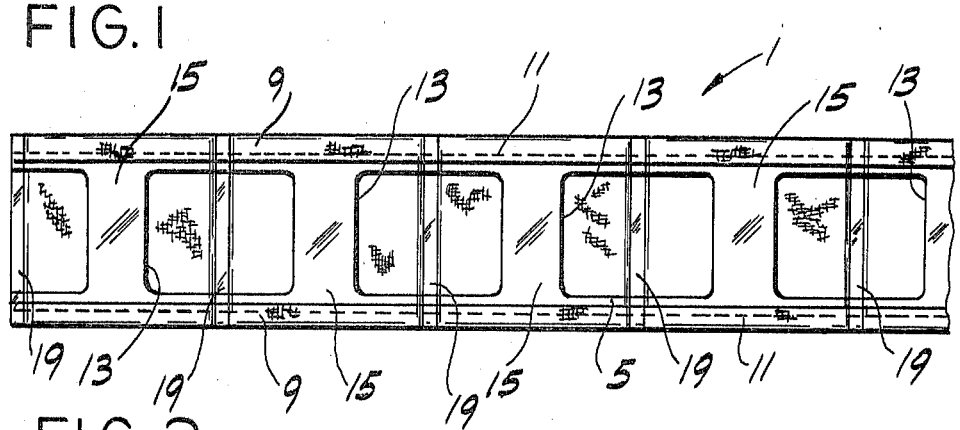
FIG. 1 is a plan view of neck pad material of this invention.
Figure 2:
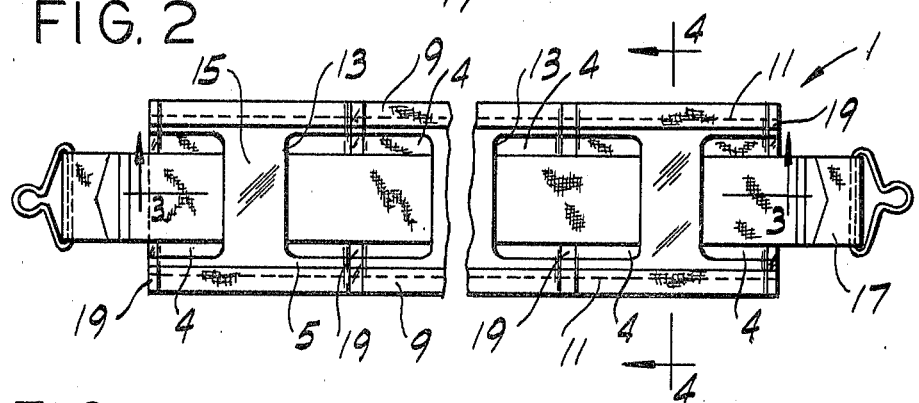
FIG. 2 is a view showing an individual pad segmented from said material and having an orthodontic appliance assembled therewith.

The strip 5 is formed with a plurality of openings 13 extending between the edges of the side margins 9 of the second outer strip 7. As shown in FIGS. 1 and 2, these openings 13 are generally square and closely spaced at equal intervals along the length of the plastic strip 5, and the relatively narrow portions 15 of the plastic strip between the openings constitute loops for the reception of an orthodontic appliance such as an elastic cervical traction brace, as indicated at 17.

Figure 3:
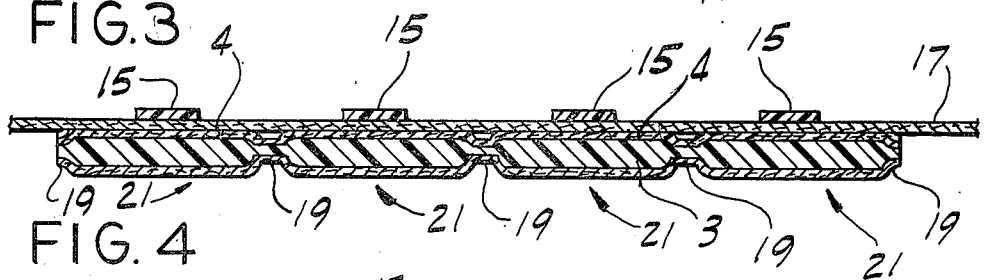
FIG. 3 is an enlarged horizontal section on line 3—3 of FIG. 2.

In accordance with this invention, the pad material 1 has relatively narrow (e.g., 3/32 in.) areas of heat seal 19 spaced at equal intervals lengthwise of the pad material 1 and extending transversely of the pad material from one edge thereof to the other. These heat seal areas 19 penetrate through all four strips 3, 4, 5, 7, which are of heat-sealable material, to seam the strips together. As shown best in FIG. 3, the pad material, and particularly the intermediate padding strip 3, is compressed and flattened out in these areas, the pad thus being divided along its length into a series of discrete relatively thick cushiony pad sections, generally designated 21, separated by the flattened-out areas of heat seal 19. Cutting transversely of the pad material 1 through these areas 19 provides a finished edge to the right end (as viewed in FIG. 1) of the severed pad and a finished edge to the left end of the pad to be next severed from the continuous length of pad material 1. Thus, it is not necessary to overstitch or otherwise finish the ends of a pad after it has been segmented.

Besides providing means for finishing the ends of a pad segmented from pad material 1, the areas of heat seal 19 also enable the pad more readily to bend when it is worn around the neck. Thus, wrinkling of the pad is reduced for increasing the comfort of the wearer. In this respect, it is preferable that the heat seal areas 19 extend transversely through openings 13 since the pad material 1 at these locations is of reduced thickness for allowing a finished pad to be easily bent to conform to the neck of the wearer.

It will be understood that the areas of heat seal 19 extending transversely of the pad material may each comprise two separate but closely spaced lines of heat seal instead of a single solid area of heat seal as shown in the drawings. In such case, a neck pad of desired length would be cut from a continuous length of pad material by cutting between the lines of heat seal, thus providing a finished edge to the severed pad and a finished edge to the pad to be next severed from the pad material.

FIGS. 5 and 6 illustrate the manufacture of neck pad material as described above. As shown, the four flexible strips 3, 4, 5, 7 forming this neck pad material are drawn from respective supply rolls 25, 27, 29, 30 by a pair of power-driven feed rollers, each designated 31, and combined on top of each other to form a composite strip 33, the lower outer strip 7 being somewhat wider than the intermediate padding strip 3, the facing strip 4 and the upper outer strip 5, all of which are generally of the same width. The composite strip 33 is continuously fed forward (to the right as viewed in FIGS. 5 and 6) between folding bars 35 at opposite sides of the strip which fold the side margins 9 of the lower outer strip 7 around the side edges of the padding and facing strips to overlie the side margins of the upper outer strip 5. The composite strip 33 is then fed through a sewing machine 36 which stitches the strip along its side margins to form lines of stitching 11. Immediately thereafter, the strip is fed between the horn 37 and anvil 39 of an ultrasonic sewing machine of the type such as shown in U.S. Pat. No. 3,666,599 and sold by Branson Sonic Power Company of Danbury, Conn. The anvil 39 is in the form of a wheel (like the wheel indicated at 24 in U.S. Pat. No. 3,666,599) with relatively narrow (e.g., 3/32 in.) raised lines 41 on its periphery for forming the areas of heat seal 19 extending transversely of the strip at intervals spaced lengthwise thereof (FIG. 7). Lines 41 extend axially on the cylindrical surface of wheel from one side of the wheel to the other and are spaced at intervals around the wheel for forming areas of seal 19 transversely of the composite strip 33 through each opening 13 in the upper outer strip 5. As the composite strip 33 passes between the horn 37 and anvil 39, with the horn ultrasonically powered, the strip is compressed and ultrasonically seamed to form, without cutting the strip, the flattened-out relatively narrow areas 19 of heat seal.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Neck pad material in the form of tape adapted to be cut to selected lengths for use with orthodontic appliances or the like comprising:

an intermediate strip of flexible compressible pad material of relatively heavy loft for providing a cushioning effect;

a first flexible outer strip on one face of the intermediate strip having a width generally corresponding to the width of the intermediate strip;

a second flexible outer strip on the other face of the intermediate strip having a width greater than the intermediate strip and the first strip and having side margins folded around the side edges of the intermediate strip and overlying the side margins of said first outer strip;

said first outer strip having openings spaced at equal intervals along the length of the strip extending between the edges of said side margins of the second outer strip, all three strips being of heat-sealable material and being seamed together along the sides of the pad material;

said pad material further having relatively narrow areas of heat seal extending transversely thereof from one edge of the pad material to the other and penetrating through said first outer strip, said intermediate strip, and said second outer strip to seam the three strips together at intervals lengthwise of the pad material, said pad material, and particularly said intermediate strip, being compressed and flattened out in said areas, the pad material thus being divided along its length into a series of discrete relatively thick cushiony pad sections separated by said flattened-out areas of heat seal, said pad material being adapted to be cut to form pads of selected lengths with finished edges by cutting transversely of the pad material through said areas.

2. Neck pad material as set forth in claim 1 wherein said strips are ultrasonically seamed together at said areas.

3. Neck pad material as set forth in claim 1 wherein said areas of heat seal are spaced at regular intervals along the length of the pad material and extend transversely through said openings in the first outer strip.

4. Neck pad material as set forth in claim 1 wherein said first outer strip is of sheet plastic and said second outer strip is a fabric strip.

5. Neck pad material as set forth in claim 4 wherein said fabric is a stretch-knit nylon fabric.

6. Neck pad material as set forth in claim 1 wherein said intermediate strip is of form rubber.

7. Neck pad material as set forth in claim 1 further comprising a facing strip of heat-sealable material between said intermediate strip and the first outer strip having a width approximately equal to the width of the intermediate strip.

8. Neck pad material as set forth in claim 7 wherein said facing strip is of stretch-knit nylon fabric.

* * * * *